(12) United States Patent
Zarfl

(10) Patent No.: US 9,504,764 B2
(45) Date of Patent: Nov. 29, 2016

(54) DISINFECTING METHOD FOR DISINFECTING A ROOM OR SURFACE, AND DISINFECTING FLUID COMPOSITION SUITABLE FOR TRANSFORMING INTO AN AEROSOL OF FLUID PARTICLES SUSPENDED IN A GAS

(76) Inventor: Hans Peter Zarfl, Wolfsberg (AT)

( * ) Notice: Subject to any disclaimer, the term of this patent is extended or adjusted under 35 U.S.C. 154(b) by 116 days.

(21) Appl. No.: 14/131,398

(22) PCT Filed: Jul. 9, 2012

(86) PCT No.: PCT/EP2012/063401
§ 371 (c)(1),
(2), (4) Date: Jan. 29, 2014

(87) PCT Pub. No.: WO2013/007688
PCT Pub. Date: Jan. 17, 2013

(65) Prior Publication Data
US 2014/0147334 A1    May 29, 2014

(30) Foreign Application Priority Data
Jul. 8, 2011 (NL) ..................................... 2007071

(51) Int. Cl.
*A61L 2/20* (2006.01)
*A01N 65/22* (2009.01)
*A01N 65/00* (2009.01)
(Continued)

(52) U.S. Cl.
CPC .................. *A61L 2/20* (2013.01); *A01N 25/06* (2013.01); *A01N 27/00* (2013.01); *A01N 65/00* (2013.01); *A01N 65/08* (2013.01); *A01N 65/22* (2013.01); *A01N 65/28* (2013.01); *A61L 2/22* (2013.01);
(Continued)

(58) Field of Classification Search
CPC ...... A01N 65/00; A01N 65/08; A01N 65/28; A01N 27/00; A01N 2300/00; A01N 65/22; A01N 25/06; A01N 65/12; A61L 2202/15; A61L 2202/25; A61L 2/20; A61L 2/22
See application file for complete search history.

(56) References Cited

U.S. PATENT DOCUMENTS 3,954,974 A    5/1976  Herzog et al.
6,296,881 B1 * 10/2001  Hata ...................... A01N 59/16
                                                        424/646
(Continued)

FOREIGN PATENT DOCUMENTS

CH              688787 A5    3/1998
CH         CH 688 787 A5    3/1998
(Continued)

OTHER PUBLICATIONS

CH 688 787 A5, Linsig Dieter et al.—English. Mar. 31, 1998.
(Continued)

*Primary Examiner* — Aradhana Sasan
(74) *Attorney, Agent, or Firm* — McKee, Voorhees & Sease, PLC

(57) ABSTRACT

Disinfecting method for disinfecting a room or a surface, comprising the steps of: a) providing a fluid comprising at least one organic compound obtainable from natural substances, wherein the organic compound is provided in an non-polar or polar medium, or in a mixture of non-polar and polar media; b) mixing the fluid with a gas such that fluid particles are suspended in the gas, and an aerosol of fluid particles is formed; c) directing a flow of the aerosol formed in step b) on said surface or into said room.

18 Claims, 1 Drawing Sheet

(51) Int. Cl.
*A01N 65/08* (2009.01)
*A01N 25/06* (2006.01)
*A01N 65/28* (2009.01)
*A61L 2/22* (2006.01)
*A01N 27/00* (2006.01)

(52) U.S. Cl.
CPC ......... *A61L 2202/15* (2013.01); *A61L 2202/25* (2013.01)

(56) References Cited

U.S. PATENT DOCUMENTS

| 2002/0068101 A1 | 6/2002 | Death |
| 2004/0009094 A1 | 1/2004 | Adiga |
| 2010/0034907 A1 | 2/2010 | Daigle |

FOREIGN PATENT DOCUMENTS

| CN | 101 406 177 A | | 4/2009 | |
| CN | 101406177 A | | 4/2009 | |
| GB | 487 855 | * | 6/1938 | ......... B01F 17/0007 |
| WO | WO 98/21307 A1 | | 5/1998 | |
| WO | 2013007688 A3 | | 1/2013 | |

OTHER PUBLICATIONS

CN 101 406 177 A, Shanghai Longmang Biiolog Techn—English. Apr. 15, 2009.
Aggag, M.E., et al., "Study of Antimicrobial Activity of Chamomile Oil", Planta Med. 22(2): pp. 140-4. Sep. 30, 1972.
Zarfl, Hans Peter, PCT/EP2012/063401 filed Sep. 7, 2012, "International Search Report" mailed Apr. 1, 2013.

* cited by examiner

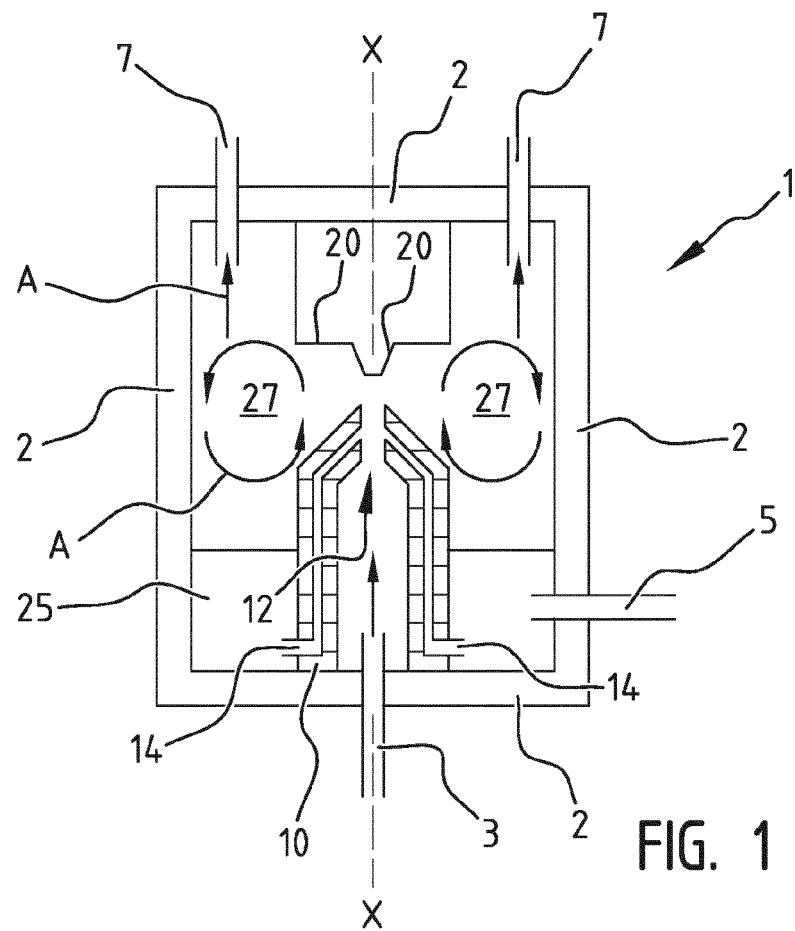
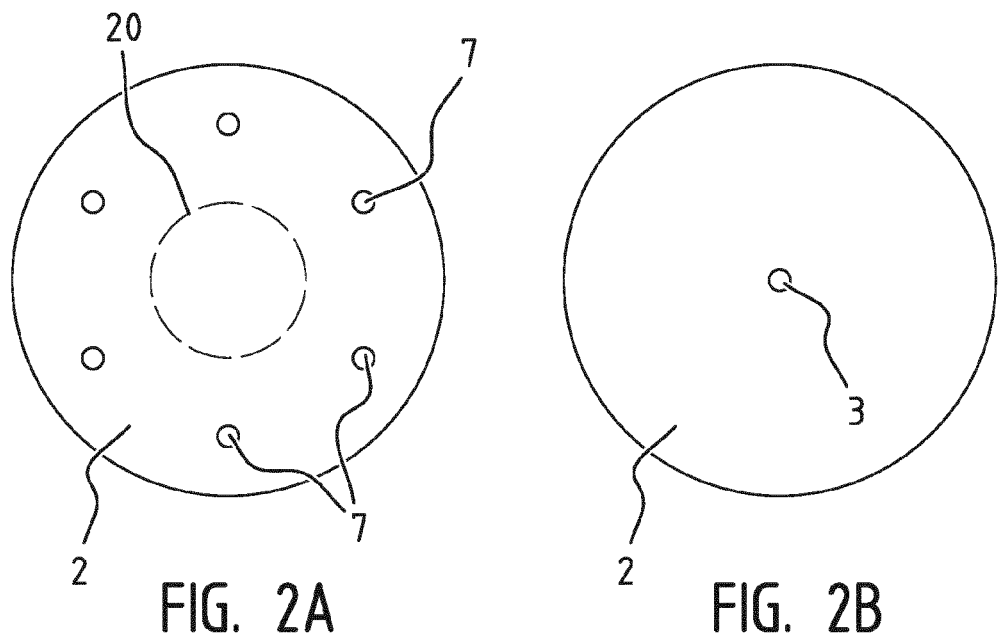

DISINFECTING METHOD FOR DISINFECTING A ROOM OR SURFACE, AND DISINFECTING FLUID COMPOSITION SUITABLE FOR TRANSFORMING INTO AN AEROSOL OF FLUID PARTICLES SUSPENDED IN A GAS

CROSS-REFERENCE TO RELATED APPLICATIONS

This is a National Phase application claiming priority to PCT/EP2012/063401 filed Jul. 9, 2012 which claims priority to NL 2007071 filed Jul. 8, 2011, all of which are herein incorporated by reference in their entireties.

The present invention is related to a disinfecting method for disinfecting a room or a surface, wherein a flow of an aerosol is used as a disinfectant.

A disinfecting method is in general aimed at inactivating microorganisms, for sanitary reasons.

It is further known to use an aerosol as a disinfectant and to apply a flow of aerosol through a room or onto a surface that should be disinfected. Thus, a room containing airborne microorganisms can be sanitized. Alternatively, a surface on which microorganisms are present can be sanitized. In both ways, any confined space designed for humans or animals can be sanitized in order to reduce or eliminate the risk of infection by microorganisms.

Most known disinfectants are however potentially harmful to humans or animals, and require a careful use thereof as well as additional safety measures before a sanitized space is used by humans or animals. This drawback is even more prominent, when the disinfectant is used in the form of an aerosol, because any unwanted absorption by a living creature (through the skin or through the respiratory tract) is more prone to occur, when compared to a disinfectant that is used in liquid form.

Furthermore, using an aerosol for disinfecting purposes has been found to be less effective in case the suspended particles in the aerosol have a particle size with a broad size distribution, i.e. the particles having a large variation in particle size.

The invention is aimed at reducing or eliminating the above drawbacks.

In addition, an attractive way of disinfecting confined spaces in which animals are kept, could significantly reduce the need for treating animals with antibiotics.

Further, the disinfected method is also aimed at sanitizing rooms which are used by humans, such as hospital rooms, the interior of aeroplanes, etc.

Therefore, the invention relates, according to a first aspect thereof, to a disinfecting method for disinfecting a room or a surface, comprising the steps of:

a) providing a fluid comprising at least one organic compound obtainable from natural substances, wherein the organic compound is provided in an non-polar or polar medium, or in a mixture of non-polar and polar media;

b) mixing the fluid with a gas such that finely divided particles of fluid are suspended in the gas, and consequently an aerosol of the suspended fluid particles is formed;

c) directing a flow of the aerosol formed in step b) on said surface or into said room.

The above method is advantageous over the prior art, because it makes use of an organic compound obtainable from natural substances, which compound has a reduced toxicity compared to known disinfectants, while at the same time being effective as a disinfectant when applied in the form of an aerosol. The organic compounds in the form of suspended particles of an aerosol are much better characterized than particles of these organic compounds used in traditional disinfection methods that are, for example, based on vaporisation of these organic substances. Thus, the wished (disinfection) effect can be induced much better and, particularly, in a quantitative way. Hence, if the disinfection method according to the present invention is used to disinfect confined spaces in which animals are kept, especially stables, the need for treating animals with antibiotics can significantly be reduced and, in turn, problems with residues of such antibiotics can be diminished or even avoided.

The non-polar medium can be an oil, preferably olive oil, and polar medium can be water, preferably water containing dissolved salts. For instance, the water may contain dissolved calcium hydroxide or sodium chloride, i.e. the water may be lime water or saline. Other useful dissolved salts are sea salts and sulphur salts.

Preferably, the overall ratio in the fluid between the total of non-polar compounds and the total of polar compounds, is between 4:1 to 1:4, more preferably between 2:1 to 1:2.

Typically, the aerosol used in the disinfecting method could be based on a fluid content of 0.1 to 15 ml fluid per cubic meter gas; for instance a fluid content of 1.0 to 3 ml fluid per cubic meter gas is used in the method.

Preferably, in the method of the invention and subsequent to step b) and prior to step c), the fluid particles of the aerosol of which the mean particle size is 1 micrometer or above, are separated from the aerosol.

The aerosol formed in step b) contains fluid particles having a broad size distribution which ranges from some nanometers to several micrometers. It has been found that in step c), wherein the aerosol is applied as a disinfectant, it is advantageous to apply an aerosol which contains particles having a mean particle size below 1 micrometer. Especially the range of a mean particle size between 10 and 100 nanometer was found to improve the effectiveness of the aerosol as a disinfectant.

Any known separation method for the aerosol may be applied, such as filtration. Another separation method, is based on the insight that when leading a flow of aerosol over deflecting surfaces, the larger particles (i.e. larger than 1 micrometer) could be separated from the smaller particles.

Separating the larger particles makes the size distribution of the remaining smaller particles narrower—the aerosol is better characterized. This in turn reduces irritation effects that might occur when less-characterized particles with a larger size distribution are used for disinfection, particularly for disinfection of confined spaces in which animals are kept. I.e. in the latter case, the well-characterized aerosol with the narrow size distribution reduces possible irritations of the animals.

Another advantage of the narrow size distribution is that deposited masses can be calculated very accurately. This enables one to precisely use only the necessary—and thus very limited—amount of particles for disinfection. In case of disinfection of the air in confined spaces in which animals are kept, especially in case of disinfection of the air in stables, the limited amount of particles further helps to avoid irritations of the animals.

Advantageously, in the method of the invention, the separated fluid particles of the aerosol are returned to the fluid that is used in step b). As such, the fluid particles which are too large for the disinfecting method, are recycled so that no fluid is lost in the process.

Preferably, in step a) of the disinfecting method of the invention, the at least one organic compound is chosen from the group consisting of: azulene, the essential oil of thyme, the essential oil of cloves, a resin from plants, derivates of the above organic compounds, and mixtures of the above organic compounds.

Azulene is a compound obtained from the distillate of camomile. The essential oils indicated above, refer to the oily substance that can be directly obtained from thyme and cloves, either by extraction or distillation processes. The resin from plants is meant as the viscous substance that is obtained from the stems of plants. A particular useful resin for the invention is Frankincense (also referred to as Olibanum) which is the aromatic resin obtained from the tree *Boswellia*.

With special preference, in step a) of the disinfecting method of the invention, the at least one organic compound is provided in a mixture of a non-polar and a polar medium, wherein the non-polar medium is an oil, preferably olive oil, and polar medium is water, preferably water containing dissolved salts. For instance, the water may contain dissolved calcium hydroxide or sodium chloride, i.e. the water may be lime water or saline. Other useful dissolved salts are sea salts and sulphur salts.

It was found that when the organic compound is provided in the above type of medium, the disinfecting effect is further enhanced.

Furthermore, it was found advantageous that in step a) of the disinfecting method of the invention, the fluid provided comprises an organic compound in water, the organic compound being present in an amount of 5-50 wt. %, preferably 10-30 wt. %, of the fluid.

The above range for the content of organic compound in the fluid, was found to be an effective concentration when used in the disinfecting method. The same favourable range is applicable to a mixture of organic compounds is used, wherein each organic compound is present in an amount of 5-50 wt. %, preferably 10-30 wt. %, of the fluid.

Especially preferred in the disinfecting method of the invention, is to use a mixture of organic compounds in water which comprises azulene, the essential oil of thyme, and the essential oil of cloves.

It was found that when applying an aerosol based on this specific mixture of organic compounds in accordance with the method of the invention, it was possible to achieve a high disinfecting effect. More specifically, it was found possible to reduce the amount of microorganisms that are suspended in the air of a confined room by 80% or more. This reduced amount of microorganisms was measured 36 hours after leading a flow of the aerosol into the confined room according to the invention.

Furthermore, it was found that the disinfecting effect of the method could be further enhanced by including a resin from plants as an organic compound in the fluid composition. A particular useful resin for the invention is Frankincense (also referred to as Olibanum) which is the aromatic resin obtained from the tree *Boswellia*.

According to another preferred variant of the disinfecting method of the invention, in step b), a mixture of the fluid and the gas is led under pressure through a nozzle, so that a spray of aerosol is discharged from the nozzle.

The use of a nozzle to form an aerosol was found both expedient and effective for the method of the invention.

In a specific variant of the disinfecting method of the invention, in step b), the gas is led under pressure through a nozzle and the fluid is admixed to the gas during passage through the nozzle, so that a spray of aerosol is discharged from the nozzle.

Such a method makes use of the Venturi-effect inside the nozzle, wherein the constricted flow of gas through the nozzle has a higher velocity which results in a reduced pressure. The reduced pressure is then effective for drawing in the fluid into the flow of gas, so that the fluid can be admixed to the gas stream, simply by providing a separate conduit for fluid which exits inside the nozzle.

When using a nozzle to form an aerosol according to the method of the invention, it is preferable that subsequent to step b) and prior to step c), the fluid particles of the aerosol of which the mean particle size is 1 micrometer or above, are separated from the aerosol by directing the spray of aerosol into a mixing chamber in which the spray is deflected by deflecting surfaces, and from which mixing chamber the aerosol is discharged via an outlet in order to perform step c).

As already explained above, the deflecting surfaces were found to be highly effective in separating larger particles (having a mean size of 1 micrometer or more) from the aerosol, which enhances the disinfecting efficacy of the method.

In a further variant of the disinfecting method of the invention, the mixing chamber and the nozzle are assembled in the form of a cartridge which further comprises a reservoir for the fluid which is in fluid communication with the nozzle and the mixing chamber. As such, the cartridge combines three functionalities needed in the method of the invention: i) the mixing of fluid and gas into an aerosol, ii) the separation of larger particles from the aerosol, iii) a reservoir for fluid to which separated particles are returned.

In a final variant of the disinfecting method of the invention, the cartridge further comprises an inlet for supplying fluid to the reservoir from a source outside of the cartridge.

As such, a disinfecting method is provided wherein a non-limited amount of fluid can be used. This is advantageous especially when large rooms are to be disinfected, and wherein the reservoir of the cartridge itself may not have the capacity for discharging the required amount of fluid.

According to a second aspect, the invention relates to a disinfecting fluid composition suitable for transforming into an aerosol of fluid particles suspended in a gas, comprising:

at least one organic compound obtainable from natural substances, which organic compound is present in a non-polar or polar medium, or in a mixture of non-polar and polar media, and wherein the at least one organic compound is chosen from the group consisting of: azulene (i.e. a distillate from camomile), the essential oil of thyme, the essential oil of cloves, a resin from plants, derivates of the above organic compounds, and mixtures of the above organic compounds.

A particular useful resin for the invention is Frankincense (also referred to as Olibanum) which is the aromatic resin obtained from the tree *Boswellia*.

When such a fluid composition is used in the disinfecting method as described above, the same advantages are achieved as already indicated: in particular, a large reduction of microorganisms in a room treated by the method of the invention is achieved.

Preferably, the disinfecting fluid composition of the invention fulfils the condition that:

the at least one organic compound is provided in a mixture of a non-polar and a polar medium, wherein the non-polar medium is an oil, preferably olive oil, and polar medium is water, preferably water containing dissolved salts.

The related advantages have already been indicated above for the method of the invention when it includes the same features.

According to a further preference, in the disinfecting fluid composition of the invention, the organic compound is present in an amount of 5-50 wt. %, preferably 10-30 wt. %, of the fluid composition.

When a mixture of organic compounds is used, the same preferred amount is applicable to each organic compound.

With particular preference, the fluid composition comprises a mixture of the organic compounds azulene, the essential oil of thyme, and the essential oil of cloves, and wherein each organic compound is present in an amount of 5-50 wt. %, preferably 10-30 wt. %, of the fluid composition.

BRIEF DESCRIPTION OF THE DRAWINGS

The invention will be further explained according to the example below, together with the appended FIGS. 1 and 2.

EXAMPLE

FIG. 1 shows a simplified view in cross-section of a cartridge to be used in the method of the invention.

FIG. 1 shows a cartridge 1 for disinfecting fluid, which has outside walls 2, which are penetrated by: an inlet 3 for pressurized gas from an outside source (not depicted), an inlet 5 for disinfecting fluid from an outside source (not depicted), and outlets 7 for discharging aerosol formed inside the cartridge 1. The cartridge 1 is of a general cylindrical shape, with the dotted line X marking the respective cylindrical axis. The bold arrows A mark the direction of streams of gas and aerosol within the cartridge 1.

Inside the cartridge 1, a conduit 10 for leading the introduced gas is provided, which narrows into a nozzle 12. The conduit 12 has internal channels 14 for leading fluid towards the nozzle 12. The channels 14 are in fluid communication with the narrow part of the nozzle passage 12, at which the gas passing through will exhibit a reduced pressure (i.e. the Venturi effect). Consequently, the fluid 25 kept in the lower part of the cartridge (i.e. the reservoir for fluid), will be drawn through channels 14 towards the nozzle 12 and mix with the gas, thus discharging a spray which is an aerosol of fluid particles in the gas. Opposite to the exit side of the nozzle 12, is a deflecting structure 20 positioned, in order to deflect the spray discharged from the nozzle 12. Grace to the deflection, a turbulent stream of aerosol is formed (depicted by the bent arrows A, which illustrate a circular flow), wherein larger fluid particles will return to the fluid 25, while smaller fluid particles (having a mean size below 1 micrometer) will remain suspended in the gas. At the same time, the aerosol spreads out over mixing chamber 27, and the smaller particles finally exit the cartridge through outlets 7. The aerosol discharged from the outlets 7 may be directly used for disinfecting a room or a surface by leading the flow of aerosol in an appropriate direction. The inlet 5 is used when an additional amount of disinfecting fluid is required inside the cartridge, so that the capacity for discharging aerosol from the cartridge is not restricted to the size of the reservoir inside.

FIGS. 2A and 2B show respectively a top and bottom view of the cartridge depicted in FIG. 1. The same features as depicted in FIG. 1, are indicated by the same reference numbers.

An example of a useful fluid composition for the disinfecting method of the invention, contains 40 wt. % thyme oil, 50 wt. % lime water, and 10 wt. % of a non-polar mixture, which includes oil of cloves, azulene and Frankincense.

Another example of a particularly useful fluid composition for the disinfecting method of the invention contains 49 wt. % thyme oil, 50 wt. % lime water, and 1 wt. % of azulene (i.e. a distillate from camomile).

The invention claimed is:

1. A disinfecting method for disinfecting a room or a surface, comprising the steps of:

a) providing a fluid comprising at least one organic compound obtainable from natural substances, wherein the organic compound is provided in a non-polar or polar medium, or in a mixture of non-polar and polar media, wherein the at least one organic compound is chosen from the group consisting of: azulene, the essential oil of thyme, the essential oil of cloves, a resin from plants, derivates of the above organic compounds, and mixtures of the above organic compounds, wherein the at least one organic compound is provided in lime water or in a mixture of a non-polar medium and lime water, wherein the organic compound is present in an amount of 5-50 wt. % of the fluid;

b) mixing the fluid with a gas such that fluid particles are suspended in the gas, and an aerosol of fluid particles is formed;

c) directing a flow of the aerosol formed in step b) on said surface or into said room.

2. The disinfecting method according to claim 1, wherein subsequent to step b) and prior to step c), the fluid particles of the aerosol of which the mean particle size is 1 micrometer or above, are separated from the aerosol.

3. The disinfecting method according to claim 2, wherein separated fluid particles of the aerosol are returned to the fluid that is used in step b).

4. The disinfecting method according to claim 1, wherein in step a): the at least one organic compound is provided in a mixture of a non-polar medium and lime water, wherein the non-polar medium is an oil.

5. The disinfecting method according to claim 1, wherein in step a): the organic compound is present in an amount of 10-30 wt. % of the fluid.

6. The disinfecting method according to claim 1, wherein in step b): a mixture of the fluid and the gas is led under pressure through a nozzle, so that a spray of aerosol is discharged from the nozzle.

7. The disinfecting method according to claim 1, wherein in step b): the gas is led under pressure through a nozzle and the fluid is admixed to the gas during passage through the nozzle, so that a spray of aerosol is discharged from the nozzle.

8. The disinfecting method according to claim 6, wherein subsequent to step b) and prior to step c), the fluid particles of the aerosol of which the mean particle size is 1 micrometer or above, are separated from the aerosol by directing the spray of aerosol into a mixing chamber in which the spray is deflected by deflecting surfaces, and from which mixing chamber the aerosol is discharged via an outlet in order to perform step c).

9. The disinfecting method according to claim 8, wherein the mixing chamber and the nozzle are assembled in the form of a cartridge which further comprises a reservoir for the fluid which is in fluid communication with the nozzle and the mixing chamber.

10. The disinfecting method according to claim 9, wherein the cartridge comprises an inlet for supplying fluid to the reservoir from a source outside of the cartridge.

11. A disinfecting fluid composition, comprising:
- at least one organic compound obtainable from natural substances, which organic compound is present in a nonpolar or polar medium, or in a mixture of non-polar and polar media,
- and wherein the at least one organic compound is chosen from the group consisting of: azulene, the essential oil of thyme, the essential oil of cloves, a resin from plants, derivates of the above organic compounds, and mixtures of the above organic compounds,
- wherein the at least one organic compound is provided in lime water or in a mixture of a non-polar medium and lime water,
- wherein the organic compound is present in an amount of 5-50 wt. % of the fluid composition.

12. The disinfecting fluid composition according to claim 11, wherein the at least one organic compound is provided in a mixture of a non-polar medium and lime water, wherein the non-polar medium is an oil.

13. The disinfecting method according to claim 7, wherein subsequent to step b) and prior to step c), the fluid particles of the aerosol of which the mean particle size is 1 micrometer or above, are separated from the aerosol by directing the spray of aerosol into a mixing chamber in which the spray is deflected by deflecting surfaces, and from which mixing chamber the aerosol is discharged via an outlet in order to perform step c).

14. The disinfecting method according to claim 13, wherein the mixing chamber and the nozzle are assembled in the form of a cartridge which further comprises a reservoir for the fluid which is in fluid communication with the nozzle and the mixing chamber.

15. The disinfecting method according to claim 14, wherein the cartridge comprises an inlet for supplying fluid to the reservoir from a source outside of the cartridge.

16. The disinfecting fluid composition according to claim 12, wherein the non-polar medium is olive oil.

17. The disinfecting fluid composition according to claim 11, wherein the organic compound is present in an amount of 10-30 wt. % of the fluid composition.

18. The disinfecting method according to claim 4, wherein the non-polar medium is olive oil.

\* \* \* \* \*